June 25, 1940. L. B. CODDINGTON Plant Pat. 405
ROSE PLANT
Filed May 15, 1939
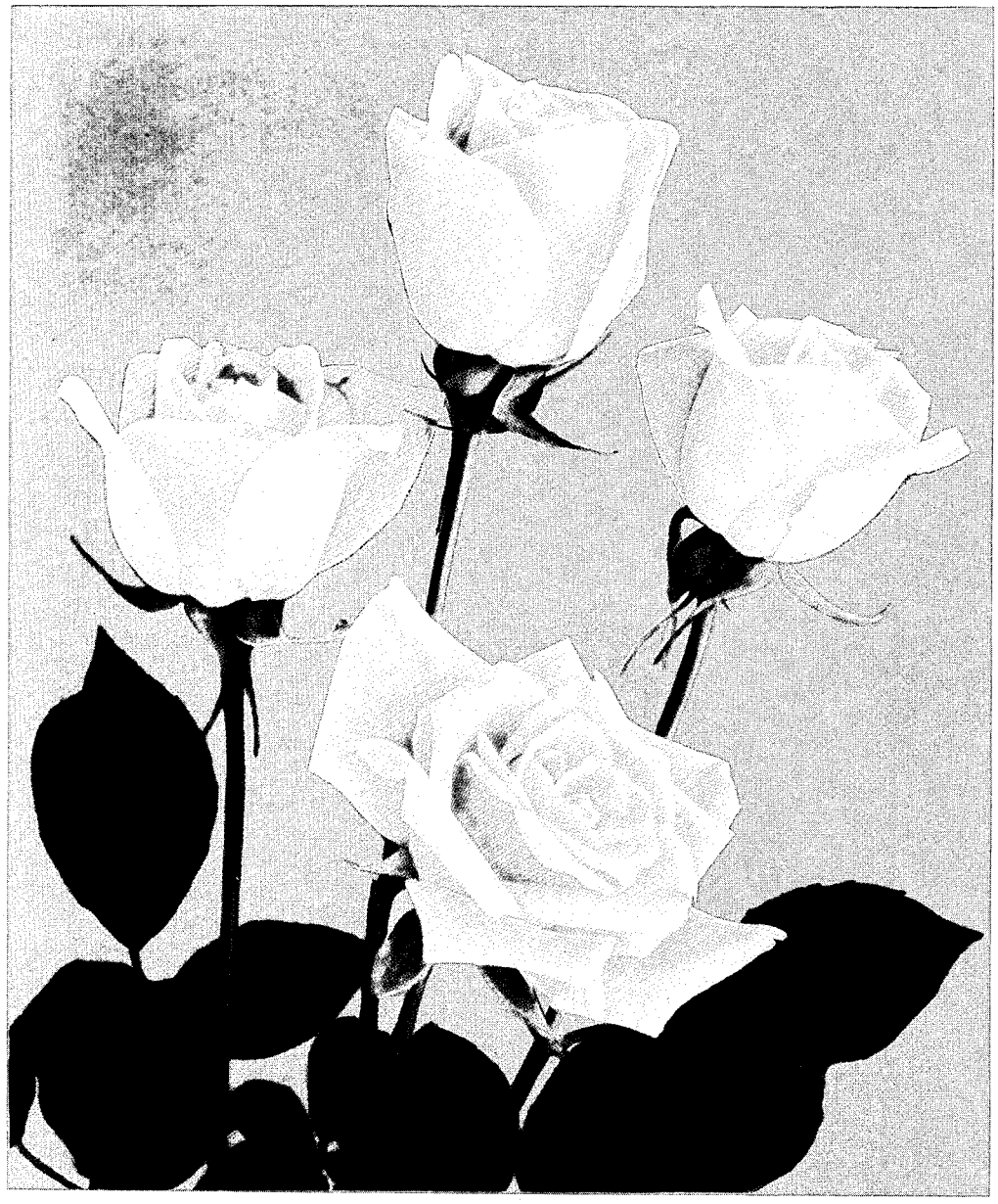
Inventor
L. B. Coddington
By Robert Robb
attorney Patented June 25, 1940

Plant Pat. 405

UNITED STATES PATENT OFFICE

405

ROSE PLANT

Lyman B. Coddington, Murray Hill, N. J., assignor to L. B. Coddington Co., Murray Hill, N. J., a corporation of New Jersey Application May 15, 1939, Serial No. 273,795

1 Claim. (Cl. 47—61)

This discovery relates to a new and distinct variety of hybrid tea rose plant, a sport of a "Joanna Hill" rose, grown and observed by me, and an excellent greenhouse forcing variety like its parent, which was originated by E. G. Hill.

In habits, growth, and other respects, this new rose resembles the Joanna Hill rose, but as to color it is essentially distinct therefrom. This color is somewhat similar to the old rose Perle des Jardin, but even more attractive and brilliant.

Asexual reproduction shows that its distinguishing characteristics hold through succeeding propagations by cuttings, grafting and budding.

The following is a detailed description of the new variety, using dictionary color terminology except where otherwise specified.

Parentage: Sport

*Parent.*—Joanna Hill.

Classification:

*Botanic and Commercial.*—Hybrid tea.

Type: Half hardy; greenhouse and out-door sport for cut flowers.

*Flower*

Observations made in a greenhouse at Murray Hill, New Jersey, in March, 1939.

Flowers borne.—Single, regular, normal, medium length stems.

Quantity of bloom.—Moderate in greenhouse.

Continuity.—Continuous, monthly blooming rose.

Fragrance.—Moderate; tea.

Bud:

*Peduncle.*—Medium length; medium stout; medium stiffness; yellowish; smooth; thorns, none.

*Before calyx breaks.* — *Size* — medium. *Form*—pointed, without appendages on the surface of the bud, with foliaceous parts extending beyond the tip of the bud equal to one-half or more of its length.

*As calyx breaks.*—*Color*—Yellow.

*As first petal opens.*—Medium size; pointed. *Color:* outside—Golden Yellow; inside—Lighter Yellow.

According to Ridgway's Color Chart, the general tone is Empire Yellow, Plate IV; base of petals, Lemon Chrome, depth of color blending through Light Cadmium to Deep Chrome, Plate III.

*Opening.*—Opens up well; controlled by greenhouse temperature.

Bloom:

*Size.*—Medium.

*Average size when fully expanded.*—Five inches to five and one-half inches.

*Petalage.*—Double; 24 to 30 petals. *Form*—high center, at first becoming open; petals tightly rolled outward, remaining so at maturity.

Petals:

*Texture.*—Thick, leathery; with inside and outside satiny.

*Shape.*—Outside—oval with apex flat. Intermediate—oval with apex flat. Inside—oval with apex flat.

*Color.*—Outside petal: outside and inside surface—Gold. Intermediate petal: outside and inside surface—Gold. inner petal: outside and inside surface—Lighter Yellow.

*General color effect.*—According to Ridgway's Color Chart, general tone of the open flower is Apricot Yellow; Plate IV: petal edges, Pinard Yellow; depths, Light Cadmium.

*Persistence.*—Persist; fading Brown Yellow.

*Lasting quality.*—Cut roses grown in greenhouse kept at living room temperatures, 5 to 7 days, in month of March.

Reproductive organs:

*Stamens.*—Many, arranged regularly.

*Filaments.*—Long, reddish, many with anthers.

*Anthers.*—Medium size; all open at once.

*Pollen.*—Abundant; lemon.

*Pistils.*—Many.

*Styles.*—Even, short, bunched.

*Stigma.*—Red.

*Ovaries.*—All enclosed in calyx.

*Hips.*—Oblong; pear shaped; green; smooth; walls dry fleshy.

*Sepals.*—Permanent; long, spear shaped.

*Seeds.*—Many, medium size.

Foliage:

*Leaves.*—Compound of 3 to 5; normal, medium size; heavy.

*Leaflets.*—Oval with apex acute, base round, margin serrate.

*Color.* — Mature: upper surface — normal green; under surface—light green-bronze. Young: upper surface—normal green; under surface—light green-bronze.

*Rachis.*—Medium. Upper side and under side—smooth.

*Stipules.*—Medium length; medium width with short points turning out at an angle of less than 45°.

*Disease resistance.*—Fairly resistant to mildew and blackspot.

Growth:

*Habit.*—Bushy, upright.

*Growth.*—Free.

*Canes.*—Medium weight.

*Main stems.*—Green. *Thorns*—few, short length, downward with narrow base. *Prickles*—few, green. *Hairs*—few, green.

*Branches.*—Dull gray. *Thorns*—few, medium length, downward. *Prickles*—few, brown. *Hairs*—few, green.

*New Shoots.*—Red. *Thorns*—few, hooked downward with broad round base. *Prickles*—none. *Hairs*—none.

I claim:

A new and distinct variety of hybrid tea rose plant, characterized as to novelty by the large size and attractive yellow color of its flower, substantially as shown and described.

LYMAN B. CODDINGTON.